United States Patent [19]  [11] Patent Number: 4,882,424
Schlossman et al.                [45] Date of Patent:   Nov. 21, 1989

[54] ACTIVATION ANTIGEN

[75] Inventors: Stuart Schlossman, Newton Center; Chikao Morimoto, Needham; Christopher Rudd, Somerville, all of Mass.

[73] Assignee: Dana-Farber Cancer Institute, Inc., Boston, Mass.

[21] Appl. No.: 49,348

[22] Filed: May 11, 1987

[51] Int. Cl.$^4$ .................. A61K 39/395; A61K 39/00; C12P 21/00
[52] U.S. Cl. .................. 530/387; 530/300; 530/351; 530/388; 530/403; 530/806; 435/68; 435/240.2; 424/85.1; 424/85.8; 424/88; 935/104; 935/108
[58] Field of Search .............. 530/387, 388, 351, 403, 530/806, 300; 935/104, 108; 435/68, 240.2; 424/88, 85.1, 85.8

[56] References Cited

U.S. PATENT DOCUMENTS

| | | | |
|---|---|---|---|
| 4,363,799 | 12/1982 | Kung et al. | 530/387 |
| 4,364,937 | 12/1982 | Kung et al. | 530/387 |
| 4,401,756 | 8/1983 | Gillis . | |
| 4,550,086 | 10/1986 | Reinherz et al. | 530/387 |
| 4,596,774 | 6/1986 | Chang et al. | 530/351 |
| 4,613,458 | 9/1986 | Okai | 530/351 |
| 4,623,622 | 11/1986 | Anderson | 435/68 |
| 4,636,463 | 1/1987 | Altman et al. | 424/88 |
| 4,683,199 | 7/1987 | Palladino | 530/351 |

OTHER PUBLICATIONS

Hoxie et al., The Journal of Immunology (Baltimore, Md., U.S.A.) vol. 137, No. 4, Issued Aug. 15, 1986, "Transient Modulation and Internalization of T4 Antigen Induced by Phorbol Esters", pp. 1194–1201.
Jan L. Ceuppens et al., "Monoclonal Antibodies to the CD5 Antigen Can Provide the Necessary Second Signal for Activation of Isolated Resting T Cells by Solid--Phase-Bound OKT3", Journal of Immunology, vol. 137, No. 6, Sept. 15, 1987, 1816–1821.
Soo Young Yang et al., "A Common Pathway for T Lymphocyte Activation Involving Both The CD3-Ti Complex and CD2 Sheep Erythrocyte Receptor Determinants", Journal of Immunology, vol. 137, No. 4, Aug. 15, 1986, 1097–1100.
Stefan C. Meuer et al., "An Alternative Pathway of T-Cell Activation" Cell, vol. 36, Apr. 1984, 897–906.
Ellis L. Reinherz et al., "The Human T Cell Receptor: Analysis with Cytotoxic T Cell Clones", Immunological Review, vol. 74, 1983, 83–112.
Alessandro Moretta et al., "Involvement of T44 Molecules In an Antigen Independent Pathway of T Cell Activation", Journal of Experimental Medicine, vol. 162, Aug. 1985, 823–838.
Toshiro Hara et al., "Human T Cell Activation", Journal of Experimental Medicine, vol. 161, Jun. 1985, 1513–1524.
Paul J. Martin et al., "Identification and Functional Characterization of Two Distinct Epitopes on the Human T Cell Surface Protein Tp50", Journal of Immunology, vol. 131, No. 1, Jul. 1983, 180–185.
Ronald Palacios et al., "Is the E Receptor on Human T Lymphocytes A 'Negative Signal Receptor'"? Journal of Immunology, vol. 129, No. 6, Dec. 1982, 2479–2593.

Primary Examiner—Margaret Moskowitz
Assistant Examiner—Abdel A. Mohamed
Attorney, Agent, or Firm—Fish & Richardson

[57] ABSTRACT

An essentially purified antigen comprising a protein present in the T-cells of *Aotus trivirgatus* having molecular weights of 140 KD and 105 KD under reducing conditions and 120 KD and 90 KD under non-reducing conditions, antibodies against this antigen, and a method of using these antibodies to activate T-cells. The antibodies are able to induce T-cell activation in synergy with phorbol myristate acetate alone and with antibody against the T $11_3$ epitope of T 11 ($CD_2$) antigen alone.

5 Claims, 1 Drawing Sheet

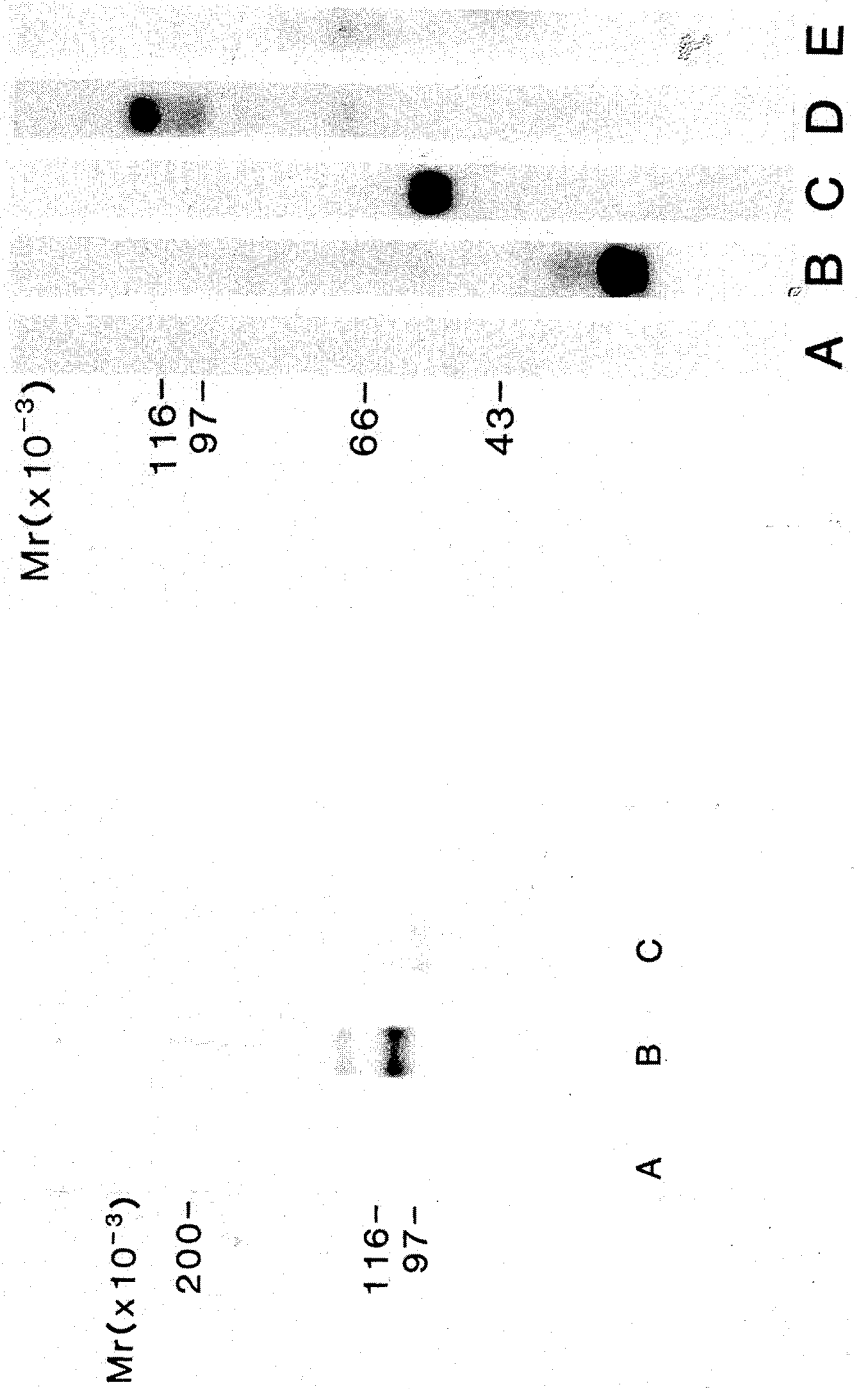

ACTIVATION ANTIGEN

BACKGROUND OF THE INVENTION

This invention is the result of work supported by the National Institute of Health, grant Nos. A112069, CA19589 and AM33713. The government has rights in the invention.

This invention relates to activation of cells involved in the immune response.

T lymphocytes play a central role in the immune response by virtue of their ability to recognize antigens with a high degree of specificity, to act as effector cells, and to regulate the nature and intensity of the immune response. The identification of specific antigens on T-cells which are involved in target cell recognition, and the availability of monoclonal antibodies which recognize such antigens, allows a detailed characterization of both the process of T-cell activation and the distinct subsets of T-cells. For example, monoclonal antibodies against the antigen-receptor complex Ti/T3 (CD3), and a combination of antibodies against epitopes on the T11 (CD2) antigen, have been found to induce the proliferation of T-cells. Another antibody, 9.3, which recognizes a distinct glycoprotein of 44,000 Daltons (D) has also been reported to stimulate cells, either alone or in conjunction with the tumor promoter 12-O-tetradecanoyl-phorbol-13-acetate (PTA). In mice, several antibodies have been used to identify other T-cell stimulating antigens, such as a product of the Ly6 locus (TAP) and the thy-1 antigen.

In addition to the target recognition role of individual structures on the surface of T-cells, evidence is accumulating to support the idea of an interaction between distinct T-cell antigens in the regulation of T-cell growth. For example, antibodies against the T3/Ti complex have been reported to block T11-induced proliferation, and vice versa. Similarly, in the absence of monocytes, combinations of non-mitogenic antibodies against either the T3 and T11 antigens or the T3 and T1 (CD5) antigens have been found to cause proliferation of resting T-cells.

SUMMARY OF THE INVENTION

This invention features a purified antigen, or fragment thereof, antibodies against this antigen, and a method of using these antibodies to activate T-cells. The antibodies are able to induce T-cell activation or proliferation in synergy with both phorbol myristate acetate (PMA) alone and with antibody against the T11$_3$ epitope (Meuer et al., 36 Cell 897, 1984) of the T11 antigen (anti-T11$_3$) alone.

In preferred embodiments, the antigen comprises at least two major polypeptides of molecular weight 140 KD and 105 KD, as determined by polycrylamide gel electrophoresis (SDS-PAGE) analysis under reducing conditions; most preferably the antigen is the protein 2Hl; the antibody is monoclonal, and is the antibody expressed by the cell line anti-2Hl, deposited with the ATCC and assigned the number HB9399.

This invention provides antibodies suitable for activation of T-cells. These antibodies can also be used to activate killer cells and to cause the appearance of elements in cells which will increase their sensitivity to other compounds, such as 1L2. They can be used to label target cells and to make such cells susceptible to killing by other cells. In vitro these antibodies are also useful for turning on the production of lymphokines, such as 1L2 and 1L4.

Other features and advantages of the invention will be apparent from the following description of the preferred embodiments thereof and from the claims.

DESCRIPTION OF THE PREFERRED EMBODIMENTS

The figures will first briefly be described.

DRAWINGS

FIGS. 1 and 2 are photographs of polyacrylamide gel electrophesis (PAGE) analysis of antigens precipitated by specific antibodies.

STRUCTURE

T-cell Antigen

The T-cell antigen is a protein found in T-cells, against which antibodies can be produced. In general, these antibodies are able to induce T-cell activation and/or T-cell proliferation in synergy with both PMA and anti-T11$_3$. That is, both PMA and anti-T11$_3$ alone can act synergistically with these antibodies to induce such activation or proliferation. Preferably, this antigen is found in T-cells of primates, most preferably of the species *Aotus trivirgatus*. In *A. trivirgatus* one such antigen is termed 2Hl and consists of two major polypeptides of molecular weight 140 KD and 105 KD.

These antigens can be purified by affinity chromatography using standard procedures, e.g., a monoclonal antibody for 2Hl can be bound to a solid phase, and proteins from disrupted T-cells passed through the column. Those which bind can be further purified by standard procedures.

After such purification, standard techniques of genetic engineering can be used to isolated genes encoding these antigens, for example, by determining the N-terminal sequence of the antigen, preparing a DNA probe capable of encoding a part of this amino acid sequence, and using this probe to detect clones in a cDNA or genomic library having DNA homologous to the probe. Such clones will generally comprise DNA encoding at least a part of the antigen. Related genes may also be isolated by this procedure and are useful for producing recombinant proteins, which can in turn be used to produce antibodies suitable in this invention, as described below.

Fragments of 2Hl or other such antigens are also useful for producing antibodies as described below. The fragments may be created by standard procedure, for example, by enzymatic digestion of total antigen, or by recombinant DNA technology. For example, a fragment of antigen can be expressed by expression of only a part of the structural gene encoding the antigen in a host cell containing an expression vector. Such fragments must act antigenically to induce antibodies which can recognize T-cells having the whole antigen.

Synergistic Antibody

A synergistic antibody is an antibody produced against the antigens or fragments described above. These antibodies recognize at least one epitope on these antigens and act in conjunction with PMA or anti-T11$_3$ to induce T-cell activation. The antibodies may be polyclonal, but preferably are monoclonal. They are produced by standard procedure using purified antigen, or fragments thereof. Most preferably the antibodies are produced against 2Hl.

The examples given below demonstrate the production of a monoclonal antibody against 2Hl of *A. trivirgatus*. These examples are not intended to be limiting to the invention and those skilled in the art will realize that other antigens and antibodies, as described above, may be isolated and utilized within the spirit of the invention.

EXAMPLE 1

Isolation of anti-2Hl

The monoclonal antibody anti-2Hl was produced by standard techniques after immunization of a Balb/c J mouse (Jackson Laboratories, Bar Harbor, ME) with cells of a T lymphocyte line derived from the New World primate species *A. trivirgatus*. Peripheral blood lymphocytes from this species were stimulated in vitro with PHA (Phytohemoagglutinin) and then maintained in continuous culture with T-cell growth factor. Spleen cells from antigen-boosted animals were harvested, fused with the HAT-sensitive myeloma line NS-1, and cultured in selective media as described by Morimoto et al., 134 *J. Immun.* 1508 and 3762, 1985. Subsequently, hybridoma cells, the supernatants of which were found to be reactive with human T lymphocytes were developed for further characterization.

Those hybridoma cultures containing antibodies reactive with human E+ cells were selected, cloned, and recloned by limiting dilution methods in the presence of feeder cells. Malignant ascites then were developed and utilized for analysis. One hybridoma antibody, anti-2Hl, is of the IgGl subclass.

The pattern of anti-2Hl reactivity and distribution of the 2Hl antigen on T-cells and thymic cells is different from anti-T11, anti-T3, and anti-9.3 and their respective antigens. For example, the fluorescence profile of T-cells and thymic cells reactive with anti-2Hl as well as their profiles following reaction with anti-T11, anti-T3, and anti-9.3 antibodies (produced as described by Reinherz et al., 19 *Cell* 821, Meuer et al. 158 *J. Exp. Med.* 988, 1983; Meuer et al., 36 *Cell* 897, 1984; and Hansen et al., 10 *Immunogentis* 247, 1980, respectively) was studied. The anti-2Hl antibody reacts with 90% of peripheral T-cells and only 10% of thymic cells. In contrast, anti-T11 antibody reacts with 95% of peripheral T-cells and 90% of thymic cells, and anti-T3 reacts with 92% of peripheral T-cells and 50% of thymic cells. Anti-9.3 antibody reacts with 85% of peripheral T-cells and 60% of thymic cells.

EXAMPLE 2

Structure of 2Hl antigen

The structure of 2Hl was determined by precipitation with antibody specific for this antigen. Briefly, Con A-stimulated peripheral blood cells (2d) were labelled by lactoperoxidase-catalysed iodination and lysed in NP40 lysis buffer for immunoprecipitation analysis. $2.0 \times 10^7$/ml cells were solubilized in NP40 lysis buffer (1 percent w/v). Nonidet P40 in 20 mM Tris-HCl buffer, pH 8.2 containing 150 mM NaCl, 1 mM EDTA, 1 mM phenyl methyl-sulphonyl fluoride (PMSF), 2.5 mM iodoacetamide, and 10 μg/ml trypsin inhibitor (Sigma Chemical Co.). Cell lysates (1 ml) were precleared overnight at 4° C. with 100 μl of 10 percent (w/v) of *Staphylococcus aureus* Cowan strain 1. The 2Hl antibody coupled to Protein A. Sepharose (~50 μg of antibody per 10 μg of beads) was added to the lysate for several hours before centrifugation and washing. Immunoprecipitates were washed in lysis buffer containing 0.1% (w/w) sodium lauryl sulphate (SDS) and twice with lysis buffer alone. Precipitates were then run on a SDS-polyacrylamide gradient gel (5–10 percent). The results are shown in FIG. 1, the lanes being respectively: (A) mouse Ig control; (B) anti-2Hl antibody under reducing conditions (5 percent v/v 2-mercaptoethanol); and (C) anti-2Hl antibody under non-reducing conditions.

Under reducing conditions, anti-2Hl antibody precipitates two subunits at approximately 140,000 and 105,000 D (FIG. 1(B)). In contrast, in a non-reduced state, the 2Hl antigen appears to migrate as two subunits of about 120,000 and 90,000 D (FIG. 1(C)). In this example each of the polypeptides appear with of the same intensity, however, the relative intensity of each band was found to vary with the cell type and experiment. For example, precipitates from the T-cell line HPB-ALL yielded a major band at 135,000 D under reducing conditions. The data indicate the presence of intrachain chain disulphide bonds within each of the 2Hl subunits. The absence of any detectable bands at a higher Mr under non-reducing conditions argues against the presence of complexes formed by interchain disulphide bonds, although some might still be present.

Anti-2Hl antibody does not react with or co-precipitate any products of the T3/Ti complex or the T11 antigen. This is shown in FIG. 2, where immunoprecipitates formed by various antibodies against these antigens were directly compared by SDS-PAGE analysis. For this analysis cells were labelled by lactoperoxidase-catalysed iodination and subjected to immuno-precipitation as described above. The lanes in FIG. 2 are respectively: (A) control mouse Ig; (B) the anti-T3 antibody (RW2 8C8); (C) the anti-T11 antibody (7T4-7E10); (D) the anti-2Hl antibody; and (E) control mouse Ig (overdeveloped). The T3 antigen includes subunits of about 19,000–20,000 D and 25,000 D (FIG. 2 (B)), (a faint amount of material at 42,000 D to 50,000 D was occasionally visualized); T11 antigen is a polypeptide at 50,000 D (FIG. 2(C)); while in contrast the anti-2Hl antibody precipitates subunits at 140,000 and 105,000 D without any detectable material in the range of either the T3/Ti or the T11 antigens (FIG. 2(D)). An additional band at about 70,000 D was seen in the anti-2Hl precipitate, however, the presence of the band in an overexposed version of the control precipitate showed this band to be non-specific (FIG. 2(E)). These data indicate that the 2Hl antigen is distinct from the T3/Ti and T11 antigens. Further, the absence of a detectable polypeptide at 44,000 D in the anti-2Hl precipitate indicates that the 2Hl antigen is distinct from the 9.3 antigen.

Further information on the structure of the 2Hl antigen was obtained by two-dimensional non-equilibrium gel (NEPHGE/SDS-PAGE) analysis of the subunits precipitated by the anti-2Hl antibody from iodinated cells. Cells were iodinated and subjected to immunoprecipitation as described above. Non-equilibrium pH gradient gel electrophoresis/polyacrylamide gel "electrophoresis" (NEPHGE/PAGE) was carried out under Servalytes (Serva Ltd.) of 20 percent (w/v) pH 2.4 and 80 percent (w/v) pH 2–11 to construct a gel containing 2% servalytes. This analysis revealed that each of the bands at 140,000 and 105,000 D is comprised of a series of discrete spots stretching over a pH range of 3–5. In addition, each of the spots was of the same approximate intensity. The presence of a series of these proteins at the acidic end of the gel is consistent with the presence of multiple sialic acid residues on each of the 2Hl subunits.

Use

The antigens described are useful for producing antibodies which can then be used to determine the number of cells bearing such antigens and thus make it possible to relate certain disease states to the lack of or excess of such antigen molecules. Further, the antigens can themselves be used to determine levels of antibodies against them within any animal or body fluid.

For example, as shown in Table 1, the reactivity of anti-2Hl antibody was determined by indirect immunofluorescence or cytofluorography. Anti-2Hl does not react with peripheral B cells, null cells and macrophages. Anti-2Hl is also unreactive with the 6 lymphoblastoid B cell lines and 4 hematopoietic lines tested. In contrast, anti-2Hl is reactive with 4 of the 7 human T-cell lines (Peer IV, HPB, HSB, SKW3) tested and weakly reacted with JM cell lines. These results indicate that the 2Hl epitope is restricted to T lymphocytes, and not expressed on other cells of hematopoietic origin. Thus, the level of such lymphocytes within any sample can be readily determined by the above described method or its equivalent.

TABLE 1

Reactivity of anti-2Hl antibody with human lymphoid and cell lines

| I. Lymphoid cells | |
|---|---|
| T-cells | + |
| B cells | − |
| Null cells | − |
| MO | − |
| II. T-cell lines | |
| Peer IV | + |
| HPB | + |
| HSB | + |
| CEM | − |
| JM | ± |
| Molt 4 | − |
| SKW3 | + |
| III. B cell lines | |
| Raji | − |
| Ramos | − |
| Daudi | − |
| Laz 388 | − |
| Laz 509 | − |
| Laz 156 | − |
| IV. Hematopoietic lines | |
| U—937 | − |
| HL-60 | − |
| K—562 | − |
| KG-1 | − |

(−) indicate less than 5 reactivity above background control, ± indicates 5–30% reactivity and (+) indicates greater than 30% reactivity.

The reactivity of anti-2Hl with activated thymic cells can also be determined. For example, the time course of 2Hl antigen expression on thymic cells after ConA and PMA activation can be examined. Representative experiments show that, after one day, 2Hl antigen expression increases dramatically on activated thymic cells and is coincident with IL-2 receptor expression on those cells. Similarly, following ConA/PMA activation, thymic cells expressed on an average a 7 fold increase in the percentage of cells with anti-2Hl reactivity (86% after activation vs. 13% before activation). This suggests that the 2Hl molecule expression is related to thymic activation. The 2Hl antigen density on peripheral T-cells, like T11 and T3 antigen density, also increases gradually after activation.

The antibodies described above are also useful for activation of T-cells using the synergistic molecules anti-T11$_3$ or PMA. These antibodies and PMA can be used in vivo to activate such cells, or in vitro to artificially turn on lymphokines such as 1L2 or 1L4. Further, parts of the antibody molecule may be combined with a tumor specific antibody such that a hybrid molecule is produced which specifically reacts with a tumor cell, and when contacted by a T-cell, activates the T-cell to kill the tumor.

For example, T-cells can be removed from a patient by standard procedure, treated in vitro with anti-2Hl and anti-T11$_3$ and then returned to the patient. This process will activate the T-cells and increase the patients immunity to disease.

It is also possible to activate peripheral T-cell in vitro. For example, monocyte depleted T-cells were cultured with monoclonal antibodies with or without PMA, and the proliferative response of the T-cells assessed. The monocyte depleted T-cells were mixed with monoclonal antibody, e.g., anti-2Hl, and TPA (sigma Chemical Co., St. Louis, MO) in round-bottomed microtiter wells (Costar, Cambridge, MA) in a 0.2 ml volume with RPMI 1640 culture medium, supplemented with 10% AB serum, 200 mM L-glutamine, 25 mM HEPES buffer (Microbiological Associates), 0.5 sodium bicarbonate, and 1% penicillin-streptomycin. At intervals after initiation of the cultures (3 days), plates were pulsed for 18 hours with tritiated thymidine ($^3$H-TdR; 1 mCi in 0.05 ml) and were harvested using a Mash II cell harvester.

As shown in Table 2, anti-2Hl, anti-T4, and anti-T11$_1$, and anti-T3 alone were not mitogenic for T-cell preparation containing 0.5% monocytes. However, in the presence of PMA, anti-2Hl and anti-T3, but not anti-T4 and anti-T11, were mitogenic for T-cells. Similarly, anti-2Hl alone was not mitogenic for T lymphocytes, even in the presence of macrophages, but following stimulation by various concentrations of anti-2Hl antibody in the presence of PMA T-cells showed a mitogenic effect, even in the presence of only a $10^{-5}$ dilution of anti-2Hl ascites with PMA (2 ng/ml).

The combination of anti-2Hl and anti-T11$_3$ is also capable of stimulating T-cell proliferation, whereas neither antibody alone had an effect on the proliferation of T-cells. For example, as shown in Table 3, the proliferative response of peripheral blood lymphocytes ($10^5$/200 μl) was assayed in triplicate in RPMI 1640 supplemented with 10% AB serum, 200 mM L-glutamine, 25 mM HEPES buffer and 1% penicillin-streptomycin. Monoclonal antibodies (1:200 dilution) were added at the start of culture after which cultures were pulsed at the designated times for 16 h with [$^3$H]-thymidine (1 μCi/well). The level of stimulation was generally about 50 to 70% less than that observed for the combination of anti-T11$_2$ and anti-T11$_3$ (see Table 3, line 4 vs. line 7, figures are in c.p.m.). These results indicate that the 2Hl antigen can also act in synergism with the T11 antigen (T11$_3$) to induce the proliferation of T-cells.

TABLE 2

Activation of T cells with PMA plus anti-2Hl antibody
$3_H$-thymidine (PMA)$^a$

| media | Exp. 1 | Exp. 2 | Exp. 3 |
|---|---|---|---|
| 2H1 | 393 ± 110 | 593 ± 230 | 634 ± 125 |
| T4 | 441 ± 124 | 278 ± 150 | 846 ± 182 |
| T11$_1$ | 371 ± 118 | 503 ± 204 | 958 ± 143 |
| T3 | 972 ± 139 | 1517 ± 360 | 1024 ± 205 |
| PMA | 978 ± 245 | 1428 ± 194 | 425 ± 90 |
| 2H1/PMA | 45467 ± 4382 | 36463 ± 5259 | 29067 ± 3004 |
| T4/PMA | 1064 ± 194 | 1528 ± 218 | 1346 ± 112 |

TABLE 2-continued

Activation of T cells with PMA plus anti-2H1 antibody
$3_H$-thymidine (PMA)[a]

| media | Exp. 1 | Exp. 2 | Exp. 3 |
| --- | --- | --- | --- |
| T11$_1$/PMA | 1214 ± 143 | 1643 ± 174 | 1156 ± 98 |
| T3/PMA | 76418 ± 5465 | 60882 ± 6498 | 96375 ± 4201 |

[a]Monocyte-depleted T-cells (1 × 10$^5$ were incubated with 1:100 dilution of antibodies (ascites) in the presence or absence of PMA (2 ng/ml). $^3$H-thymidine uptake were measured after 3 days.
[b]Values were expressed as the mean ± SMEM of triplicate samples.

TABLE 3

Activation of T lymphocytes by
the combination of anti-2H1
and anti-T11$_3$ antibodies

| Culture addition | Exp. 1 | Exp. 2 |
| --- | --- | --- |
| Control (media) | 14 | 92 |
| T11$_2$ | 307 | 462 |
| T11$_3$ | 502 | 3798 |
| T11$_2$ + T11$_3$ | 97724 | 53443 |
| 2H1 | 1027 | 942 |
| 2H1 + T11$_2$ | 153 | 145 |
| 2H1 + T11$_3$ | 29641 | 33229 |

Deposit

Anti-2Hl has been deposited with the American Type Culture Collection and given ATCC accession Number HB9399. This culture will be maintained for 30 years, 5 years after the request for any one strain, or until the end of the term of the patent issued, whichever is the longer. Applicants' assignee, DANA FARBER CANCER INSTITUTE, acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR §1.14 and 35 USC §112.

Other embodiments are within the following claims.

We claim:

1. An antibody which specifically binds to a protein antigen present in the T-cells of *Aotus trivirgatus*, said antigen comprising two major polypeptides having molecular weights determined by SDS-PAGE analysis of 140 KD and 105 KD respectively under reducing conditions and 120 KD and 90 KD respectively under non-reducing conditions and having isoelectric points of pH 3–5 by non-equilibrium pH gradient gel electrophoresis/polyacrylamide gel electrophoresis analysis, said antibody producing, in combination with phorbol myristate acetate or with anti-T11$_3$, proliferation of T-cells bound to said antibody.

2. The antibody of claim 1, said antibody being monoclonal.

3. The antibody of claim 2, said antibody being expressed by the cell line anti-2Hl, deposited in the ATCC and assigned the number HB9399.

4. A method for activating T-cells comprising mixing said cells with the antibody of claim 1, 2, or 3, and with phorbol myristate acetate or anti-T11$_3$ for a time and under conditions sufficient to stimulate T-cell proliferation.

5. An essentially purified antigen which specifically binds the anti-2Hl monoclonal antibody comprising a protein identical to a protein present in the T-cells of *Aotus trivirgatus* comprising two major polypeptides having molecular weights determined by SDS-PAGE analysis of 140 KD and 105 KD respectively under reducing conditions and 120 KD and 90 KD respectively under non-reducing conditions and having isoelectric points of pH 3–5 by non-equilibrium pH gradient gel electrophoresis/polyacrylamide gel electrophoresis analysis.

* * * * *

UNITED STATES PATENT AND TRADEMARK OFFICE
CERTIFICATE OF CORRECTION

PATENT NO. : 4,882,424

DATED : November 21, 1989

INVENTOR(S) : Stuart Schlossman, Chikao Morimoto, Christopher Rudd

It is certified that error appears in the above-identified patent and that said Letters Patent is hereby corrected as shown below:

Col. 2, line 13, "electrophesis" should be --electrophoresis--.

Col. 3, line 40, "Immunogentis" should be --Immunogenetics--.

Col. 5, line 49, "5" should be --5%--.

Col. 7, line 18, "14" should be --154--.

Signed and Sealed this

Twenty-fifth Day of December, 1990

Attest:

HARRY F. MANBECK, JR.

Attesting Officer

Commissioner of Patents and Trademarks